United States Patent
Schaller

[11] Patent Number: 5,817,107
[45] Date of Patent: Oct. 6, 1998

[54] GRASPING INSTRUMENT WITH A GUIDED-ON, ATTACHABLE MODIFIED KNOT PUSHER

[76] Inventor: Günter Schaller, Am Lüsbuhl 32A, D-79110 Freiburg, Germany

[21] Appl. No.: 772,461

[22] Filed: Dec. 23, 1996

[30] Foreign Application Priority Data

Dec. 28, 1995 [DE] Germany .................. 195 49 361.3
Jul. 31, 1996 [DE] Germany .................. 196 30 863.1

[51] Int. Cl.⁶ ............................................ A61B 17/04
[52] U.S. Cl. .................................. 606/139; 606/139
[58] Field of Search .................. 606/139, 148; 289/17

[56] References Cited

U.S. PATENT DOCUMENTS

| | | | |
|---|---|---|---|
| 5,292,327 | 3/1994 | Dodd et al. | 606/148 |
| 5,324,298 | 6/1994 | Phillips et al. | 606/148 |
| 5,382,258 | 1/1995 | Chow | 606/148 |
| 5,391,176 | 2/1995 | de la Torre | 606/148 |
| 5,403,330 | 4/1995 | Tuason | 606/148 |
| 5,454,820 | 10/1995 | Kammerer | 606/148 |
| 5,472,446 | 12/1995 | de la Torre | 606/148 |
| 5,527,323 | 6/1996 | Jervis et al. | 606/148 |
| 5,601,576 | 2/1997 | Garrison | 606/148 |

*Primary Examiner*—Gary Jackson
*Attorney, Agent, or Firm*—Jeffrey M. Kaden; Norbert P. Holler; Gottlieb, Rackman & Reisman, P.C.

[57] ABSTRACT

A grasping instrument provided with a guided-on, attachable, modified knot pusher and designed for positioning and fixing a knot in a suture at a remote surgical location. The knot is easily formed outside the patient's abdominal cavity by hand and fixed on the instrument tip. After intra-abdominal insertion, the knot pusher serves to forward the knot on the thread and to immediately tighten it without any troublesome instrument change being required. A spring-loaded mechanism enables the applied force to be predetermined for achieving a reliable knot strength.

29 Claims, 4 Drawing Sheets

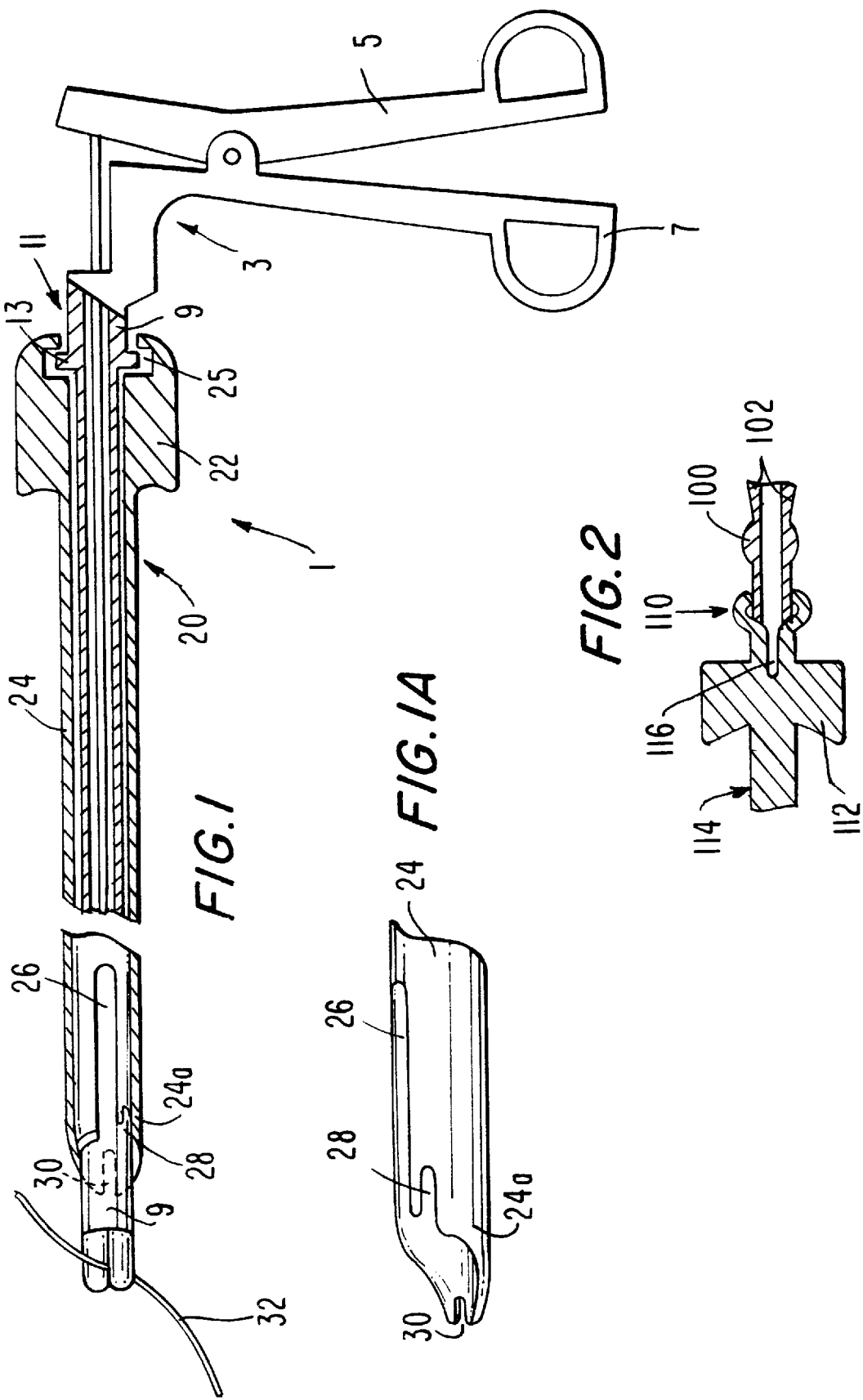

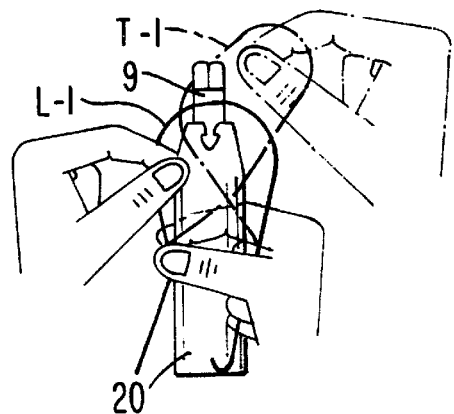
FIG. 5.1
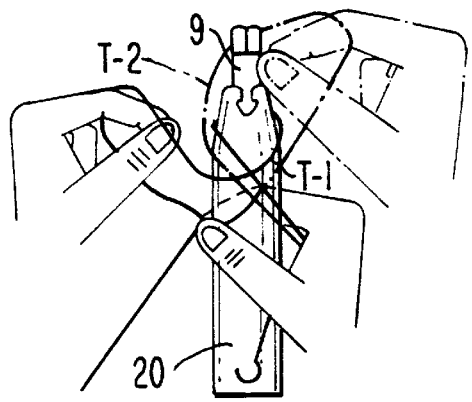
FIG. 5.2
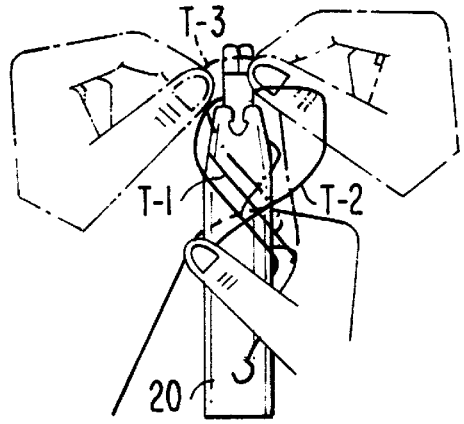
FIG. 5.3
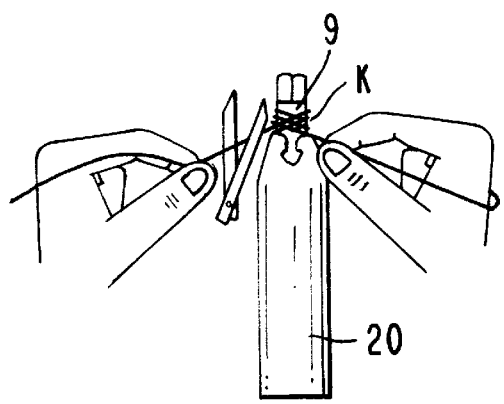
FIG. 5.4

GRASPING INSTRUMENT WITH A GUIDED-ON, ATTACHABLE MODIFIED KNOT PUSHER

BACKGROUND OF THE INVENTION (1) Field of the Invention

The present invention relates to a surgical instrument for tying a knot in a length of a suture in a remote surgical area. In the laparoscopic technique, knot pushers are know to be separately used to tighten a knot that was tied extracorporally. Small incisions are made and the remote surgical site is accessed through cannulas and tubes. The extracorporal tying of the knot in a remote location outside the body and the following displacement of the loose knot along the length of the suture material is complicated in a darkened room and entails a troublesome instrument change.

(2) Description of the Related Art

U.S. Pat. No. 5,391,176, for example, discloses that instruments adapted to be used to form throws of materials in a length of suture material outside the patient's body and to later intracorporally tie a knot in the suture material are known. As described in that patent and its related U.S. Pat. Nos. 5,472,446 and 5,527,323, the particular type of instrument there shown for delivering a knot to a remote surgical location includes a hollow rod with a slot at the distal end. A removable handle can be attached to the rod. An interior bore is present to introduce a grasper. The rod carries distally at least one loop in the length of a suture to later be pulled onto the thread near the needle to form a knot. The end of the thread is preferably located at and fixed extracorporally to the proximal end of the hollow rod. Additionally a mechanism is incorporated to retract an inner rod, carrying thread material, to release preformed loops on the thread. No safe closure of the knot is possible without the use of a knot pusher. The size of the needle is restricted and the traction on the tissue is high. Closing and tightening the knot has to be done with two grasping instruments. Due to their bending, the true force applied on the thread is difficult to judge.

SUMMARY OF THE INVENTION

The present invention contemplates that to avoid intracorporal knot formation, a knot can easily be made extracorporally by hand and be placed on the tip of the grasping instrument. A safe, strong attachment of the knot is needed to allow manipulations after inserting it into the patient's abdominal cavity. Then the knot has to be pushed forward from the instrument on the thread to form the loop. For that purpose, a knot pusher with an interior bore is guided on the grasping instrument, the diameter of the bore being such as to generally match the exterior diameter of the grasping instrument for enabling the grasping instrument to slipfit, i.e., to be adapted for sliding, reciprocating movements, therein. When later pushing the knot from the instrument, the knot pusher has to directly slide on the tube of the instrument to avoid jamming the thread. The grasping instrument is slightly longer to give space for the knot placement. To allow the intracorporal manipulation without displacement of the knot by the knot pusher, caused by the friction of the rubber sealing of the trocars, the handgrip of the instrument and grip of the knot pusher additionally have coupling means to be attached to each other, selectively connected or disconnected during the application of suture and ligation.

As a first modification of the instrument according to the present invention, to enable the instrument to freely accommodate a plurality of needle sizes, the knot pusher has an axial slot therein extending proximally from its distal end to allow the needle to bypass from the interior bore, when traction is applied on the thread by the grasping instrument.

As a second modification, a notch is provided at the distal tip of the knot pusher to facilitate the extracorporal formation of the knot, fixing the thread near the tip of the grasping instrument.

As a preferred embodiment, the coupling means at the side of the instrument handgrip is a longitudinal enlargement with a conical shape, projecting distally on the tube, to hold the corresponding cavity in the grip of the knot pusher by friction. With this construction, the grip can be made of plastic material. In another embodiment, the handgrip of the instrument carries a ball-like enlargement to fit into a lock-in cavity in the grip of the knot pusher, having at least one slot to be expanded with a certain force.

Scientifically the forces applied to tighten knots are studied for different braided and monofilament thread materials to create reliable knot strength. The forces in newtons are measured by a spring-loaded tensiometer. In another embodiment, the above described knot pusher allows to measure the force applied to tighten the knot. In one embodiment the grip slides on the tube, a metal spring transmitting the pushing force between them.

Along the tube of the knot pusher an abutment or bearing holds the spring to transmit the pushing force. The spring is guided proximally on the tube. The grip is hollow to slide over the spring and bearing, projecting distally to be stabilized, when the spring is loose. Under pressure on the grip of the knot pusher the tube projects proximally over the grip. Markings are put on the tube corresponding to the actual force applied. The markings can also be at the abutment. After validation during the manufacturing process, a measurement in newtons can be made possible. The spring can transmit the force either under pressure or under traction, yet a different attachment of the spring is needed for each case. Rubber, plastic or other distortable elastomer materials can transmit the applied force.

Along the tube of the knot pusher, electrical pressure transducers such as piezo crystals can be used to measure the force. The metal spring however allows steam autoclavation.

The knot formation is done as follows: An easy technique allows to quickly form three loops in the length of any thread material, creating a knot to hold on the instrument tip. By holding the thread in one hand, forming a loop, and fixing the grasping instrument additionally with one finger, the other hand can form two loops by turning each of them through 180° and placing them over the instrument tip. A third loop is guided through the second loop and is placed over the instrument tip. The resulting knot is tightened on the instrument tip near the tip before the distal end of the knot pusher. One end of the thread is cut short, leaving a longer second end for a ligation or carrying the needle for a suture.

With the same construction and the same surgical techniques, the instrument set can also be used in open surgery.

BRIEF DESCRIPTION OF THE DRAWINGS

FIG. 1 shows the grasping instrument with the guided-on knot pusher, pursuant to the invention, in a partly sectional longitudinal side view.

FIG. 1A shows a side view, drawn to a somewhat enlarged scale and as seen from a different angle, of a part of the knot pusher of the grasping instrument of FIG. 1.

FIG. 2 shows a detailed view, not drawn to scale, of the coupling means between the handgrip of the instrument and grip of the knot pusher in accordance with another.

FIGS. 5.1 to 5.4 show the four steps of the method of extracorporally forming a knot on the instrument tip.

DESCRIPTION OF THE PREFERRED EMBODIMENTS

Figure 3:
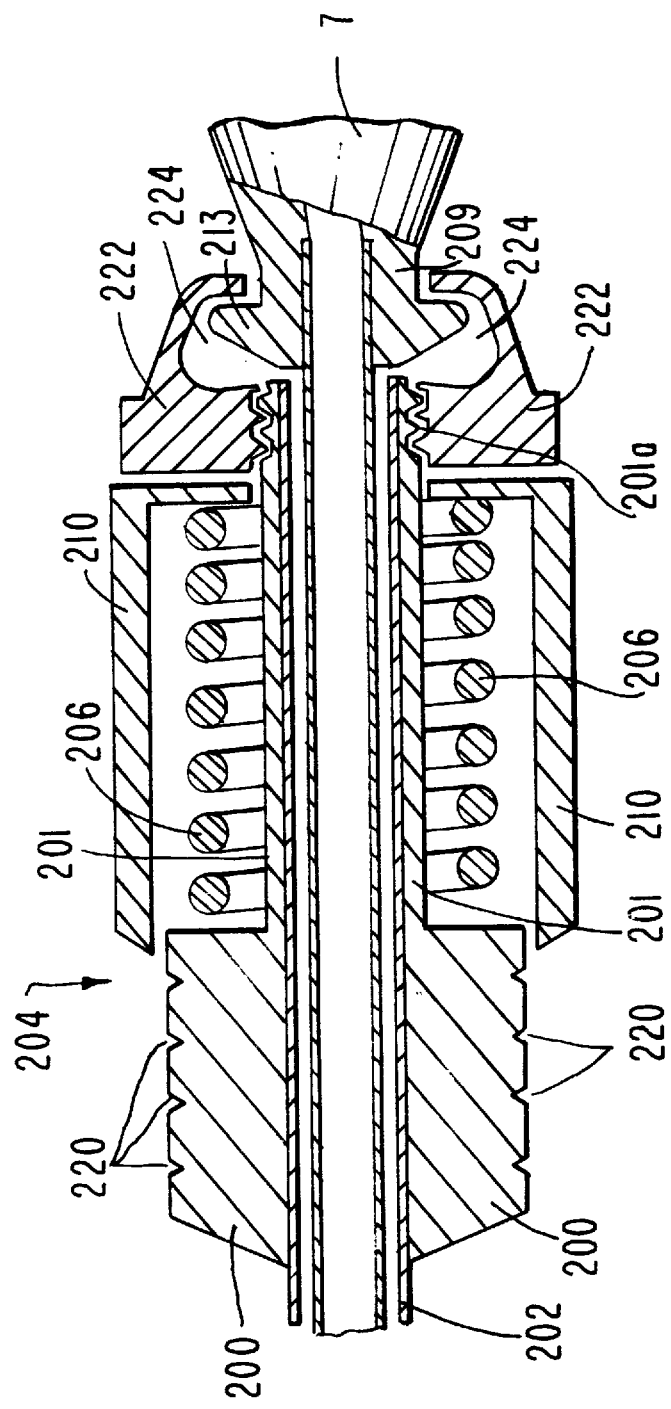
FIG. 3 shows a longitudinal cross-sectional side view of the instrument with the spring loaded construction between the grip and the tube of the knot pusher.

In the embodiment of FIG. 1, the grasping instrument 1 has a handgrip 3 with a movable part 5 and a frame part 7. From the frame part 7 projects a tube 9 which coaxially supports a reciprocally slidable knot pusher 20 in the form of a tube 24 having a grip 22 at its proximal end. The handgrip 3 and the knot pusher 20 are releasably connected to each other by a coupling means 11 which is constituted by a disc-like enlargement or flange 13 formed on the tube 9 and engageable in a correspondingly sized and shaped lock-in cavity 25 provided in the proximal end of the grip 22. The tube 24 in its distal end or tip region 24a has an axial slot 26 which extends proximally from the tip. A notch 28 in the tip region 24a near the slot 26 allows fixing the thread during the formation of the knot. The tube 24 in its tip end region 24a further has a slot 30, preferably opposite slot 26, which serves to hold back the knot to apply tension to tighten it, when the grasping instrument is pulling the thread 32.

In the embodiment of FIG. 2, the attachment or coupling between the grasping instrument and the knot pusher is achieved by the ball-like enlargement 100 at the frame part 102 and the lock-in cavity 110 of the grip 112 of knot pusher 114. The lock-in cavity has a slot 116 so as to be able to expand under a certain force to disconnect the coupling means.

In the embodiment of FIG. 3, the abutment 200, formed at the distal end of a cylinder 201, for a spring 206 is present along the tube 202 of the knot pusher 204. The spring 206 is guided proximally on the cylinder 201. The abutment 200 carries markings 220. The hollow grip 210 of knot pusher 204 distally slides over abutment 200 and spring 206. Under axial pressure on grip 210, the markings 220 are subsequently covered. The coupling means between the handgrip 7 of the grasping instrument and the knot pusher is constituted by a generally conical enlargement 213 on the tube 209 of the handgrip and an expandable cavity 224 provided in the proximal end of an internally threaded disc 222 screwed onto the externally threaded proximal end 201a of the cylinder 201, the enlargement 213 being selectively engageable in and disengageable from the cavity 224. The disc 222 also prevents the hollow grip 210 from sliding off the cylinder 201 when the knot pusher 204 is removed backwards from the abdominal cavity.

Figure 4:
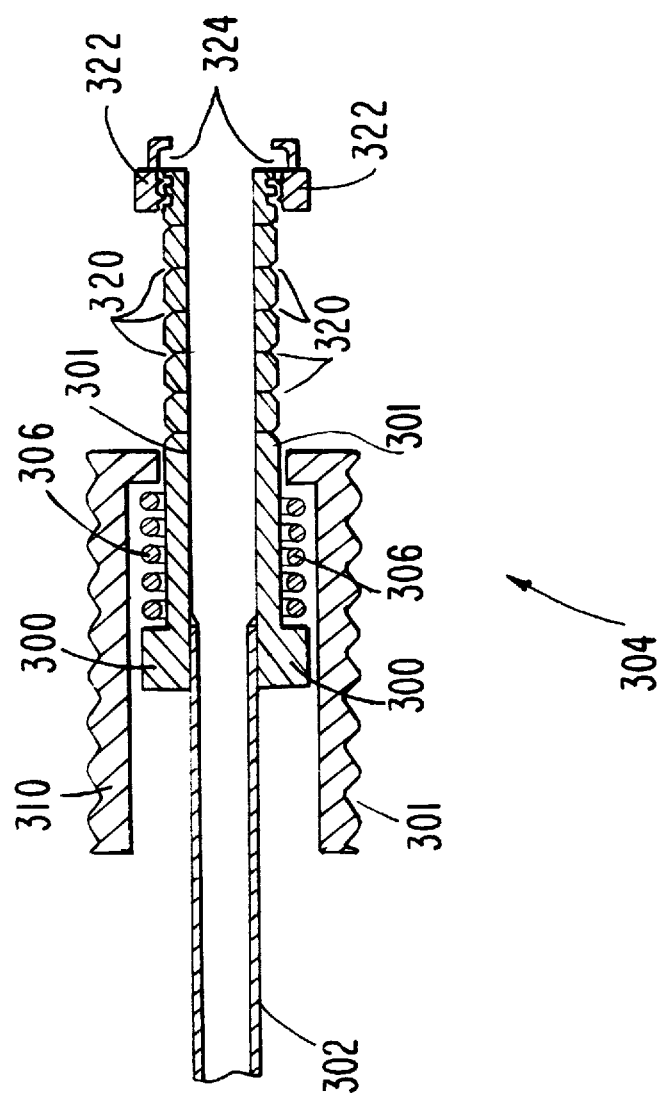
FIG. 4 shows a similar view with the spring under pressure and the proximal markings visible proximal the grip of the knot pusher.

In the embodiment of FIG. 4, the abutment 300, formed at the distal end of the cylinder 301, for a spring 306 is connected to the proximal end of tube 302 of the knot pusher 304. The spring 306 is guided on the cylinder 301 proximally of the abutment 300. The cylinder 301 carries markings 320. The hollow grip 310 of knot pusher 304 distally slides over abutment 300 and spring 306. Under axial pressure on grip 310, the cylinder 301 with markings 320 is visible proximal the grip 310. The attachable screw-on disc 322 with the expandable cavity 324, which is a part of the coupling means between the handgrip of the grasping instrument and the knot pusher, prevents the hollow grip 310 from sliding off the cylinder 301 when the knot pusher 304 is removed backwards from the abdominal cavity.

In FIGS. 5.1 to 5.4, the extracorporal formation of the knot to be used with the above-described device is illustrated schematically as being effected in four related steps:

Initially one hand holds the thread in the form of a starting loop L-1 and additionally fixes the device with at least one finger, the other hand later forming a first throw of the knot T-1 by turning the starting L-1 loop of the thread through 180° and placing it over the tip of the grasping instrument 9 (FIG. 5.1), then forming a second throw of the knot T-2 over the instrument tip with the same technique at the side of the thread end (FIG. 5.2), and finally guiding a third throw of the knot T-3, created at the side of the needle or ligation, through the second throw T-2 and placing it over the instrument tip (FIG. 5.3), the resulting knot K being tightened on the instrument near the tip thereof distally of the distal end of the knot pusher 20 (FIG. 5.4).

While the present invention has been described by preference to a specific embodiment, it should be understood that modifications and variations of the invention may be constructed without departing from the scope of the invention defined in the following claims.

What is claimed is:

1. A device for forming and tightening a knot in a suture thread when performing an endoscopic suture or ligation, comprising:

a grasping instrument including a handgrip having a frame part and a movable part, and a first tube having distal and proximal ends and extending distally from said frame part of said handgrip, said first tube in its proximal end region near its junction with said frame part being provided with a first coupling member; and a modified knot pusher supported by said grasping instrument, said knot pusher including a second tube having distal and proximal ends and an interior bore of a diameter dimensioned to enable said second tube to internally receive said first tube for reciprocal relative sliding movement between said first and second tubes, a grip member associated with said second tube adjacent said proximal end of said second tube for enabling said second tube to be moved distally along said first tube to apply force to a knot when the same is being tightened, said second tube at said proximal end thereof being provided with a second coupling member adapted to interengage with said first coupling member, said first and second coupling members constituting coupling means for selectively connecting said knot pusher to and disconnecting it from said handgrip of said grasping instrument, and said second tube in its distal end region being provided with an axial slot extending proximally from said distal end of said second tube to permit a needle to bypass said interior bore laterally.

2. A device as claimed in claim 1, wherein said first coupling member of said grasping instrument is in the form of a conical peripheral enlargement projecting distally from said frame part of said handgrip and coaxially encircling said proximal end region of said first tube.

3. A device as claimed in claim 1, wherein said first coupling member of said grasping instrument is in the form of a ball-like or disc-like external enlargement of said first tube.

4. A device as claimed in claim 1, wherein said first coupling member of said grasping instrument is in the form of a screw tap or a bayonet fitting.

5. A device as claimed in claim 1, wherein said second coupling member of said modified knot pusher is in the form of a conical bore.

6. A device as claimed in claim 1, wherein said second coupling member of said modified knot pusher is in the form of an expandable lock-in cavity with at least one slot.

7. A device as claimed in claim 1, wherein said second coupling member of said modified knot pusher is in the form of a screw tap or bayonet fitting.

8. A device as claimed in claim 1, wherein said second tube of said modified knot pusher is provided at said distal end region of said second tube with a notch to facilitate the formation of a knot on said first tube of said grasping instrument at the distal end region of said first tube.

9. A device as claimed in claim 1, wherein said grip member is loosely mounted on said second tube of said knot pusher, and a metal spring is operatively interposed between said grip member and an adjunct of said second tube for transmitting, by either a tensile or a compressive distortion of said spring, a force applied between said grip member and said second tube during the tightening of a knot.

10. A device as claimed in claim 1, wherein said grip member is loosely mounted on said second tube of said knot pusher, and a resilient body of a material selected from the group consisting of metal, rubber, plastics and elastomeric materials is operatively interposed between said grip member and an adjunct of said second tube for transmitting, by either a tensile or a compressive distortion of said body, a force applied between said grip member and said second tube during the tightening of a knot.

11. A device as claimed in claim 1, wherein said grip member is loosely mounted on said second tube of said knot pusher, an abutment is provided peripherally on said second tube, and a metal spring is operatively interposed between said grip member and said abutment for transmitting, by either a tensile or a compressive distortion of said spring, a force applied between said grip member and said second tube during the tightening of a knot.

12. A device as claimed in claim 11, wherein said grip member is hollow and is dimensioned to slide distally over said abutment and said spring.

13. A device as claimed in claim 12, wherein markings indicative of applied forces are provided on said abutment.

14. A device as claimed in claim 11, wherein a cylinder having a proximal end and a distal end is affixed in exteriorly surrounding relation to said proximal end region of said second tube of said knot pusher, with said proximal end of said cylinder located even with said proximal end of said second tube, and said abutment for said spring is in the form of an enlargement of said cylinder located distally of said proximal end of said second tube.

15. A device as claimed in claim 14, wherein said grip member of said second tube of said knot pusher is hollow and is dimensioned to slide distally over said abutment, said cylinder and said spring.

16. A device as claimed in claim 15, wherein markings indicative of applied forces are provided on said abutment.

17. A device as claimed in claim 16, wherein a stop member is releasably attached to said cylinder at said proximal end of the latter for preventing said grip member from sliding off said cylinder when said knot pusher is withdrawn from a patient's abdominal cavity.

18. A device as claimed in claim 17, wherein said cylinder is provided at its proximal end region with external threads, said stop member is a ring provided in a distal region thereof with internal threads and is screwed onto said cylinder, and said second coupling means is arranged in a proximal region of said stop member.

19. A device as claimed in claim 11, wherein a cylinder having a proximal end and a distal end is affixed at said distal end thereof coaxially to said proximal end of said second tube of said knot pusher, and said abutment for said spring is in the form of an enlargement of said cylinder located at the juncture of said proximal end of said second tube and said distal end of said cylinder.

20. A device as claimed in claim 19, wherein said grip member of said second tube of said knot pusher is hollow and is dimensioned to slide distally over said abutment, said cylinder and said spring.

21. A device as claimed in claim 20, wherein markings indicative of applied forces are provided on said cylinder.

22. A device as claimed in claim 21, wherein a stop member is releasably attached to said cylinder at said proximal end of the latter for preventing said grip member from sliding off said cylinder when said knot pusher is withdrawn from a patient's abdominal cavity.

23. A device as claimed in claim 22, wherein said cylinder is provided at its proximal end region with external threads, said stop member is a ring provided in a distal region thereof with internal threads and is screwed onto said cylinder, and said second coupling means is arranged in a proximal region of said stop member.

24. A modified knot pusher for use with a grasping instrument which is designed for performing an endoscopic suture or ligation and includes a handgrip having a frame part and a movable part, a first tube having distal and proximal ends and extending distally from said frame part of said handgrip, and first coupling means provided on said first tube in its proximal end region near its junction with said frame part;

said knot pusher comprising a second tube having distal and proximal ends and an interior bore of a diameter dimensioned to enable said second tube to internally receive said first tube for reciprocal relative sliding movement between said first and second tubes, a grip member associated with said second tube adjacent said proximal end of said second tube for enabling said second tube to be moved distally along said first tube to apply force to a knot when the same is being tightened, second coupling means provided at said proximal end of said second tube for permitting a selective interengagement of said second coupling means with and disengagement thereof from said first coupling means for selectively connecting said knot pusher to and disconnecting it from said handgrip of said grasping instrument, and an axial slot provided in said second tube at the distal end region of said second tube and extending proximally from said distal end of said second tube to permit a needle to bypass said interior bore laterally.

25. A modified knot pusher as claimed in claim 24, wherein said second tube is provided at said distal end region thereof with a notch to facilitate the formation of a knot on said first tube of said grasping instrument at the distal end region of said first tube.

26. A modified knot pusher as claimed in claim 24, wherein said grip member is loosely mounted on said second tube, and a metal spring is operatively interposed between said grip member and an adjunct of said second tube for transmitting, by either a tensile or a compressive distortion of said spring, a force applied between said grip member and said second tube during the tightening of a knot.

27. A modified knot pusher as claimed in claim 24, wherein said grip member is loosely mounted on said second tube, and a resilient body of a material selected from the group consisting of metal, rubber, plastics and elastomeric materials is operatively interposed between said grip member and an adjunct of said second tube for transmitting, by either a tensile or a compressive distortion of said body, a force applied between said grip member and said second tube during the tightening of a knot.

28. A modified knot pusher as claimed in claim 24, wherein the modified knot pusher in its entirety is made of a synthetic plastic material and is disposable after use on one patient.

29. A method of forming and tightening a knot in a surgical thread with the aid of a device having a distal end and including a grasping instrument and a modified knot pusher, as claimed in claim 1, when used in the performance of an endoscopic suture or ligation, comprising the steps of:

- holding the thread in the form of a starting loop in one hand and simultaneously holding said device steady with one finger;

- thereafter turning said starting loop through 180° with the other hand so as to form a first throw of the knot, and placing said first throw of the knot over the distal end or tip of said device;

- thereafter forming a second throw of the knot at the side of the thread end in the same manner as the formation of said first throw of the knot, and placing said second throw of the knot over the distal end or tip of said device;

- then forming a third throw of the knot at the side of the needle or ligation, feeding said third throw of the knot through said second throw of the knot, and placing said third throw of the knot over the distal end or tip of said device; and

- tightening the resulting knot on said device distally of the distal end of said knot pusher.

* * * * *